United States Patent
Shimotoyodome et al.

(10) Patent No.: US 9,445,987 B2
(45) Date of Patent: Sep. 20, 2016

(54) CERAMIDE PRODUCTION ENHANCER AND MOISTURIZER

(75) Inventors: Yoshie Shimotoyodome, Haga-gun (JP); Shotaro Ito, Haga-gun (JP); Yoshiya Sugai, Haga-gun (JP); Hiroshi Hashimoto, Haga-gun (JP); Junko Ishikawa, Haga-gun (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 13/499,810

(22) PCT Filed: Sep. 27, 2010

(86) PCT No.: PCT/JP2010/066698
§ 371 (c)(1),
(2), (4) Date: Apr. 2, 2012

(87) PCT Pub. No.: WO2011/043212
PCT Pub. Date: Apr. 14, 2011

(65) Prior Publication Data
US 2012/0196841 A1    Aug. 2, 2012

(30) Foreign Application Priority Data

Oct. 5, 2009 (JP) .................. 2009-231847
Apr. 28, 2010 (JP) .................. 2010-103651

(51) Int. Cl.
| | |
|---|---|
| A61K 31/58 | (2006.01) |
| A61K 8/97 | (2006.01) |
| A23L 1/00 | (2006.01) |
| A23L 1/30 | (2006.01) |
| A61K 8/63 | (2006.01) |
| A61K 36/185 | (2006.01) |
| A61K 36/28 | (2006.01) |
| A61K 36/48 | (2006.01) |
| A61Q 19/00 | (2006.01) |
| C07D 493/08 | (2006.01) |

(52) U.S. Cl.
CPC .............. *A61K 8/97* (2013.01); *A23L 1/0029* (2013.01); *A23L 1/3002* (2013.01); *A61K 8/63* (2013.01); *A61K 31/58* (2013.01); *A61K 36/185* (2013.01); *A61K 36/28* (2013.01); *A61K 36/48* (2013.01); *A61Q 19/00* (2013.01); *C07D 493/08* (2013.01)

(58) Field of Classification Search
None
See application file for complete search history.

(56) References Cited

U.S. PATENT DOCUMENTS

| | | | |
|---|---|---|---|
| 6,866,856 B2 | 3/2005 | Lu et al. | |
| 2004/0127556 A1* | 7/2004 | Lu et al. | 514/468 |
| 2008/0206175 A1 | 8/2008 | Chung | |
| 2010/0317637 A1 | 12/2010 | Lee et al. | |
| 2011/0117038 A1 | 5/2011 | Kawasaki et al. | |

FOREIGN PATENT DOCUMENTS

| | | |
|---|---|---|
| EP | 0 993 822 A1 | 4/2000 |
| JP | 1986-291515 A | 12/1986 |
| JP | 05-155738 A | 6/1993 |
| JP | 07-138180 A | 5/1995 |
| JP | 07-157420 A | 6/1995 |
| JP | 07-238011 A | 9/1995 |
| JP | 08-012561 A | 1/1996 |
| JP | 11-116492 A | 4/1999 |
| JP | 2000-086495 A | 3/2000 |
| JP | 2000-319120 A | 11/2000 |
| JP | 2000-336024 A | 12/2000 |
| JP | 2004-210743 A | 7/2004 |
| JP | 2005-060366 A | 3/2005 |
| JP | 2005-194246 A | 7/2005 |
| JP | 2006-514657 A | 5/2006 |
| JP | 2006-290749 A | 10/2006 |
| JP | 2006-327988 A | 12/2006 |
| JP | 2008-150314 A | 7/2008 |
| JP | 2008-156325 A | 7/2008 |

(Continued)

OTHER PUBLICATIONS

International Search Report (ISR) for PCT/JP2010/066698, I.A. fd: Sep. 27, 2010, mailed Dec. 28, 2010 from the Japanese Patent Office, Tokyo, Japan.

(Continued)

*Primary Examiner* — Dennis Heyer
*Assistant Examiner* — Daniel M Podgorski
(74) *Attorney, Agent, or Firm* — Sterne, Kessler, Goldstein & Fox P.L.L.C.

(57) ABSTRACT

A ceramide production enhancer and a moisturizer containing, as an active ingredient, an extract of at least one plant selected from the group consisting of *Chenopodium hybridum*, *Melia toosendan*, *Indigofera tinctoria*, *Cirsium japonicum*, *Catalpa ovate*, and *Tagetes erecta*, or a compound represented by the following Formula (1):

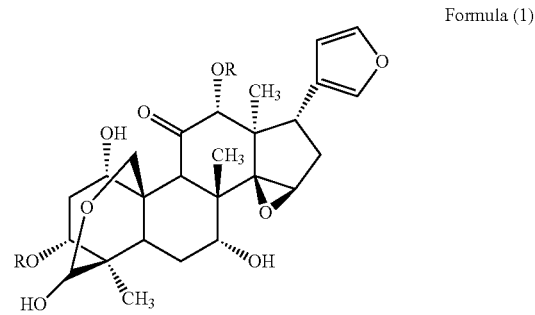

Formula (1)

wherein, R represents an acyl group having 1 to 5 carbon atom(s).

14 Claims, 1 Drawing Sheet

(56) References Cited

FOREIGN PATENT DOCUMENTS

| | | |
|---|---|---|
| JP | 2008-266156 A | 11/2008 |
| JP | 2010-070497 A | 4/2010 |
| JP | 2010-070498 A | 4/2010 |
| JP | 2010-070499 A | 4/2010 |
| JP | 2011-079754 A | 4/2011 |
| KR | 2001-0093861 | 10/2001 |
| WO | WO 2004/026273 A1 | 4/2004 |
| WO | WO 2004/060326 A1 | 7/2004 |
| WO | WO 2007/094312 A1 | 8/2007 |
| WO | WO 2007145276 A1 * | 12/2007 |
| WO | WO 2011/062078 a1 | 5/2011 |

OTHER PUBLICATIONS

International Preliminary Report on Patentability (IPRP), Chapter I of the Patent Cooperation Treaty, including the Written Opinion for PCT/JP2010/066698, I.A. fd: Sep. 27, 2010, issued May 8, 2012, from the International Bureau of WIPO, Geneva, Switzerland.

Benaiges, A, "Quinoa quality," Soap, Perfumery & Cosmetics 71: 53, 55-56 (1998), United Trade Press, London, England and reprinted from HighBeam Business, http://business.highbeam.com/3783/article-1G1-20766149/quinoa-quality/print, Cengage Learning, Independence, KY.

Hamada S et al., "Biology, immunology, and cariogenicity of *Streptococcus* mutans," Microbiol. Mol. Biol. Rev. 44: 331-384 (Jun. 1980), American Society for Microbiology, Washington, DC.

Roccamo, AM et al., "Cells defective in sphingolipids biosynthesis express low amounts of muscle nicotinic acetylcholine receptor," Eur J Neurosci 11(5): 1615-1623, (May 1999), Oxford University Press, Oxford, UK.

Zhaolong Li, "New Use of Chinaberry (*Melia azedarach*)," Today Science & Technology, 1998, issue 7, p. 31, Editorial Department of Science and Technology Today, Zhejiang Institute of Science and Technology Information, Zhejiang Province, China.

Extended European search report including the supplementary European search report and European search opinion, for EP appication No. 10821883.5, dated Mar. 25, 2014, European Patent Office, Munich, Germany.

Zhang, B et al., "Growth inhibition and apoptosis-induced effect on human cancer cells of toosendanin, a tritpenoid derivative from Chinese traditional medicine," Investigational New Drugs, Dec. 2005; 23(6): 547-553, Springer, New York.

Excerpted file history, U.S. Appl. No. 12/939,349, Non-Final Rejection mailed Oct. 22, 2014, and Request for Continued Examination, with Amendment and Arguments, filed Nov. 6, 2013.

Prosecution history of U.S. Appl. No. 12/939,349 through Oct. 29, 2013.

King, RA et al., "Albinism," Chapter 147 in The Metabolic and Molecular Bases of Inherited Disease, seventh edition, Scriver, CR et als. eds., vol. 3, pp. 4353-4392 (1995), McGraw-Hill, Inc., United States.

Miyachi, Y. et al., "External preparation for whitening," excerpt from: Advanced Cosmetic Dermatology No. 1—Skin Whitening Strategy, Part IV: Pharmacology and Clinical Practice for Skin-Lightening Agents, pp. 95-115, Nankodo Co., Ltd., Japan.

Ong, ES et al., "Qualitative and quantitative analysis of toosendanin in Melia toosendan Sieb. Et Zucc (Meliaceae) with liquid chromatography/tandem mass spectrometry," Rapid Commun Mass Spectrom 21(4): 589-598 (Jan. 2007), John Wiley and Sons Ltd, Chichester, England.

Wakabayashi, W. et al., "*Melia toosendan* extract attenuates ET-1-induced PKC signaling in pigment cells and ET-1-stimulated pigmentation in human epidermal equivalents," Abstract OP5, 22nd Meeting of the Japanese Society for Pigment Cell Research, (JSPCR—2009), Dec. 5-6, 2009, Fukuoka, Japan, Pigment Cell & Melanoma Research, 22: 907-917, doi: 10.1111/j.1755-148X.2009.00638.x (published online Oct. 14, 2009), John Wiley & Sons A/S, Denmark.

Wrathall, JR et al., "Suppression of pigmentation in mouse melanoma cells by 5-bromodeoxyuridine: Effects on tyrosinase activity and melanosome formation," J. Cell Biol. 57: 406-423 (May 1973), Rockefeller University Press, United States.

Xing, Z et al., "Effects of Toosendanin on Several Enzyme Systems of the Cabbage Worm *Pieris rapae* L.," Kunchong Xuebao 35:171-177 (May 1992).

Extended European search report including the supplementary European search report and the European search opinion, for EP Appl. No. 10831473.3, mailed Apr. 23, 2013, European Patent Office Rijswijk, Netherlands.

International search Report for PCT/JP2010/069827, mailed Feb. 15, 2011, Japanes Patent Office, Tokyo, Japan.

International Preliminary Report on Patentability (IPRP), Chapter I of the Patent Cooperation Treaty, including the Written Opinion for PCT/JP2010/069827, I.A. fd: Nov. 8, 2010, issued Jun. 12, 2012, from the International Bureau of WIPO, Geneva Switzerland.

Iyengar, B. "Modulation of Melanocytic Activity by Acetylcholine," Acta Anat 1989; 136:139-141.

Gong, J. et al., ("Zhi wu mei rong yan jiu gai kuang"), Journal of Shandong University of Traditional Chines Medicine, Sep. 2009; 33(5):438-439, Shandong University, Jinen, China.

Han, Guang, "Topical treatment of cracking of hand and foot with *Melia toosendan*," Journal of External Therapy of Traditional Chinese Medicine, 1996, issue 5, p. 16, Shanxi Medical Association, Shanxi Province, China.

China Liu, Hong-ya et al., "Identification of the Toosendanin in *Fructus toosendan* by TLC," Lishizhen Medicine and Materia Medica Research, 2008, 19(7): 1674, Huangshi Shi publisher, China.

Excerpted file history U.S. Appl. No. 12/939,349: Amendment and Reply filed Mar. 19, 2015, and Applicant Initiated Interview Summary (PTOL-413), mail room date Jan. 27, 2015.

Excerpted file history U.S. Appl. No. 12/939,349: Final Office action mailed Jul. 2, 2015, by the United States Patent and Trademark Office, Alexandria, VA.

Excerpted file history U.S. Appl. No. 12/939,349: Notice of Abandonment mailed Jan. 8, 2016, by the United States Patent and Trademark Office, Alexandria, VA.

* cited by examiner

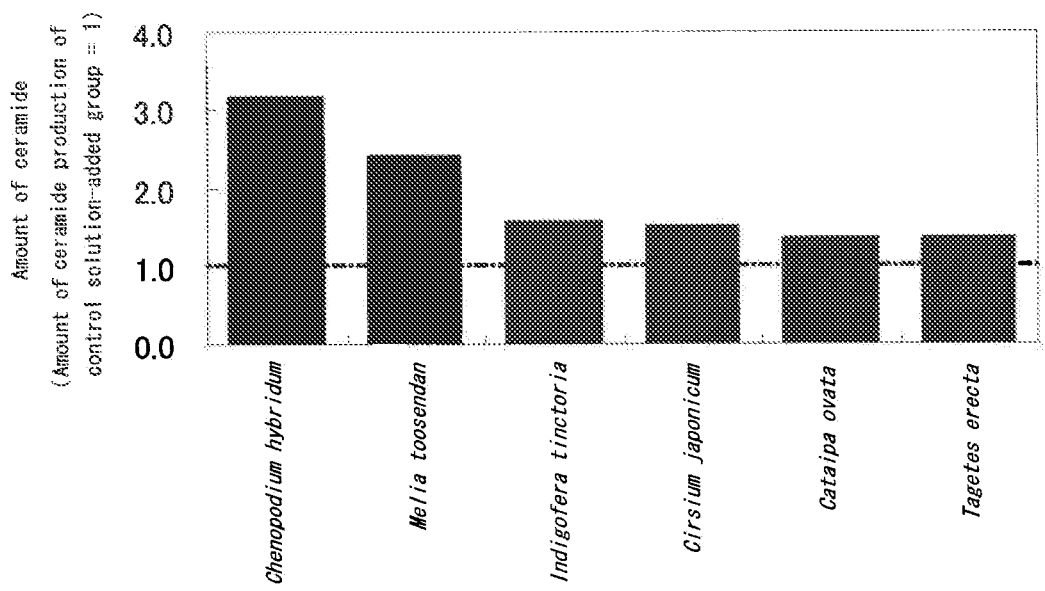

CERAMIDE PRODUCTION ENHANCER AND MOISTURIZER

TECHNICAL FIELD

The present invention relates to a ceramide production enhancer and a moisturizer.

BACKGROUND ART

Although ceramides, which are one class of sphingolipids, are lipids that are available only in an extremely small amount with respect to the whole body, in the stratum corneum which is the outermost layer of the skin, ceramides are contained more than half of the amount of lipids, and play the important roles in the water holding function and barrier function of the skin. These ceramides are produced in the epidermal cells, then secreted to form a lamellar structure in intercellular spaces of the stratum corneum, and they maintain the stratum corneum functions. It has been extensively reported that, in skin diseases such as dry skin, rough skin, atopic dermatitis, senile xerosis and psoriasis, normal metabolism of ceramides is interfered and the amount of ceramides in the stratum corneum decreases, followed by occurring deterioration of the water holding function, barrier function and the like of the skin.

There have been attempts to develop methods of supplying decreased ceramides from an external source, but at present, the effects of the methods are not necessarily sufficient.

SUMMARY OF INVENTION

The present invention is contemplated for providing a ceramide production enhancer having an effect of enhancing ceramide production at a higher level. Further, the present invention is contemplated for providing a moisturizer excellent in a function to enhance ceramide production.

In view of the purposes described above, the inventors of the present invention have made extensive studies. As a result, they have found out that plant extracts of *Chenopodium hybridum*, *Melia toosendan*, *Indigofera tinctoria*, *Cirsium japonicum*, *Catalpa ovata* and *Tagetes erecta* have a function to enhance ceramide production at a higher level.

Further, the inventors of the present invention found out that a compound represented by the following Formula (1) has a function to enhance ceramide production at a higher level, and obtained a finding that this compound is useful as a novel moisture-retaining component. The present invention has been completed based on these findings.

The present invention provides the following means:

(1) A ceramide production enhancer, containing an extract of at least one plant selected from the group consisting of *Chenopodium hybridum*, *Melia toosendan*, *Indigofera tinctoria*, *Cirsium japonicum*, *Catalpa ovata* and *Tagetes erecta* as an active ingredient.

(2) A moisturizer, containing an extract of at least one plant selected from the group consisting of *Chenopodium hybridum*, *Melia toosendan*, *Indigofera tinctoria*, *Cirsium japonicum*, *Catalpa ovata* and *Tagetes erecta* as an active ingredient.

(3) A ceramide production enhancer, containing a compound represented by the following Formula (1) as an active ingredient:

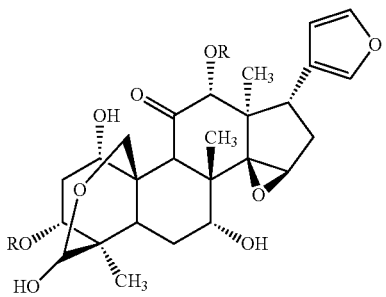

Formula (1)

wherein R represents an acyl group having 1 to 5 carbon atom(s).

(4) A moisturizer, containing the compound represented by the above Formula (1) as an active ingredient.

(5) An extract of at least one plant selected from the group consisting of *Chenopodium hybridum*, *Melia toosendan*, *Indigofera tinctoria*, *Cirsium japonicum*, *Catalpa ovata* and *Tagetes erecta* for use in the enhancement of ceramide production.

(6) An extract of at least one plant selected from the group consisting of *Chenopodium hybridum*, *Melia toosendan*, *Indigofera tinctoria*, *Cirsium japonicum*, *Catalpa ovata* and *Tagetes erecta* for use in the moisture retention.

(7) The compound represented by the above Formula (1) for use in the enhancement of ceramide production.

(8) The compound represented by the above Formula (1) for use in the moisture retention.

(9) A method of enhancing ceramide production, including applying an extract of at least one plant selected from the group consisting of *Chenopodium hybridum*, *Melia toosendan*, *Indigofera tinctoria*, *Cirsium japonicum*, *Catalpa ovata* and *Tagetes erecta* to a skin.

(10) A method of retaining moisture, including applying an extract of at least one plant selected from the group consisting of *Chenopodium hybridum*, *Melia toosendan*, *Indigofera tinctoria*, *Cirsium japonicum*, *Catalpa ovata* and *Tagetes erecta* to a skin.

(11) A method of enhancing ceramide production, including applying the compound represented by the above Formula (1) to a skin.

(12) A method of retaining moisture, including applying the compound represented by the above Formula (1) to a skin.

(13) Use of an extract of at least one plant selected from the group consisting of *Chenopodium hybridum*, *Melia toosendan*, *Indigofera tinctoria*, *Cirsium japonicum*, *Catalpa ovata* and *Tagetes erecta* for the preparation of a medicament having an effect of retaining moisture based on enhancing ceramide production.

(14) Use of the compound represented by the above Formula (1) for the preparation of a medicament having an effect of retaining moisture based on enhancing ceramide production.

According to the present invention, a ceramide production enhancer can be provided. Further, according to the present invention, a moisturizer excellent in a function to enhance ceramide production can be provided.

Other and further features and advantages of the present invention will appear more fully from the following description.

BRIEF DESCRIPTION OF THE DRAWINGS

FIG. 1 is a diagram showing the amounts of ceramides when using the extracts of *Chenopodium hybridum*, *Melia* toosendan, *Indigofera tinctoria*, *Cirsium japonicum*, *Catalpa ovata*, and *Tagetes erecta*.

MODE FOR CARRYING OUT INVENTION

Hereinafter, the present invention is described in detail.

The ceramide production enhancer and the moisturizer of the present invention contain, as an active ingredient, an extract of at least one plant selected from the group consisting of *Chenopodium hybridum*, *Melia toosendan*, *Indigofera tinctoria*, *Cirsium japonicum*, *Catalpa ovata* and *Tagetes erecta*, or the compound represented by the above Formula (1). The extract and the compound have a function to enhance ceramide production at a higher level.

First, the ceramide production enhancer and the moisturizer of the present invention, both of which contain plant extracts as active ingredients, are explained.

According to the present invention, *Chenopodium hybridum* is a plant which belongs to the family Rubiaceae, genus *Chenopodium*. This plant has been traditionally used as a dye, and in addition to that, as medicinal effects of this plant, a sendative action has been known.

*Melia toosendan* is a plant which belongs to the family Meliaceae, genus *Melia*, As medicinal effects of this plant, a sedative action, an analgesic action and an anthelmintic action have been known. Furthermore, a dried fruit of *Melia toosendan* has been used as an herbal medicine called Senrenshi.

*Indigofera tinctoria* (alias: Nanbanai) is a plant which belongs to the family Polygonaceae, genus *Indigofera*. This plant has been traditionally used as a dye or a pigment, and a product obtained by drying the pigment present in the leaves is called Seitai.

*Cirsium japonicum* is a plant which belongs to the family Asteraceae, genus *Cirsium*. As medicinal effects of this plant, a diuretic action, a neuralgia-relieving action and the like have been known. A dried root of this plant is used as an herbal medicine called Taikei.

*Catalpa ovate* is a plant which belongs to the family Bignoniaceae, genus *Catalpa*. As a medicinal effect of this plant, a diuretic action has been known. A dried fruit of this plant is called Shijitsu, and has been used as an herbal medicine.

*Tagetes erecta* (alias: Senju chrysanthemum) is a plant which belongs to the family Asteraceae, genus *Tagetes*. As medicinal effects of this plant, an eye disease preventive action and an eyestrain-relieving action have been known.

With respect to *Chenopodium hybridum*, *Melia toosendan*, *Indigofera tinctoria*, *Cirsium japonicum*, *Catalpa ovata*, and *Tagetes erecta* used in the present invention, any and all parts of the plant can be used. For example, any one or more selected from whole tree of the plant, whole grass of the plant, or any part (roots, rhizomes, trunks, branches, stems, leaves, barks, tree sap, tree resin, flowers, fruits, seeds, pericarp, shell, germ, spike, heartwood, and the like), and combinations thereof, can be used.

In the present invention, among the various parts of the plants mentioned above, it is preferable to obtain an extract particularly from the parts described below.

In order to obtain an extract of *Chenopodium hybridum*, it is preferable to extract the whole grass of *Chenopodium hybridum*.

In order to obtain an extract of *Melia toosendan*, it is preferable to extract the fruits of *Melia toosendan*. Further, in the case of extracting the fruits of *Melia toosendan*, Senrenshi, which has been used as an herbal medicine, can be used.

In order to obtain an extract of *Indigofera tinctoria*, it is preferable to extract the leaves of *Indigofera tinctoria*, and it is also preferable to use the pigment obtained from the leaves of *Indigofera tinctoria*.

In order to obtain an extract of *Cirsium japonicum*, it is preferable to extract the roots of *Cirsium japonicum*. Further, in the case of extracting the roots of *Cirsium japonicum*, Taikei, which has been used as an herbal medicine, can be used.

In order to obtain an extract of *Catalpa ovata*, it is preferable to extract the fruits of *Catalpa ovata*. Further, in the case of extracting the fruits of *Catalpa ovata*, Shijitsu, which has been used as an herbal medicine, can be used.

In order to obtain an extract of *Tagetes erecta*, it is preferable to extract the flowers of *Tagetes erecta*.

There is no particular limitation on the method for preparing extracts of *Chenopodium hybridum*, *Melia toosendan*, *Indigofera tinctoria*, *Cirsium japonicum*, *Catalpa ovata* and *Tagetes erecta* that are used in the present invention, and extracts can be obtained by extracting the plants by conventional methods. Specifically, juice extracts obtained by pressed extraction of dried products prepared by drying the plants described above or ground products thereof and the like; steam distillates; crude extracts obtained by using various extraction solvents; fractions of the extracts obtained by purifying the crude extracts using various chromatographic techniques such as partition chromatography and column chromatography; and the like can be used as the extracts of the present invention.

The plants described above can be supplied to the extraction process in an unprocessed state, but in order to enhance the extraction efficiency, it is also preferable to apply processes such as drying, fine cutting and grinding. Also, in the present invention, the extracts, steam distillates, pressed products and the like described above may be used such that any one of them is used alone, or two or more kinds are used in combination. Among them, as the plant extract of the present invention, it is more preferable to use an extract obtained from a dried product prepared by drying the plants, or a ground product thereof, by using an extraction solvent.

As the extraction solvent, any of polar solvents and non-polar solvents can be used, and mixtures of these solvents can also be used. Examples include water; alcohols such as methanol, ethanol, propanol and butanol; polyhydric alcohols such as ethylene glycol, propylene glycol, and butylene glycol; ketones such as acetone and methyl ethyl ketone; esters such as methyl acetate and ethyl acetate; linear and cyclic ethers such as tetrahydrofuran and diethyl ether; polyethers such as polyethylene glycol; halogenated hydrocarbons such as dichloromethane, chloroform, and carbon tetrachloride; hydrocarbons such as hexane, cyclohexane and petroleum ether; aromatic hydrocarbons such as benzene and toluene; pyridines; supercritical carbon dioxide; oils and fats, waxes, and other oils. Alternatively, a mixture combining two or more kinds of the solvents described above can be used as the extraction solvent. Among these, it is preferable to use water, an alcohol, a water-alcohol mixed liquid, propylene glycol, or butylene glycol, and it is more preferable to use an aqueous ethanol solution.

The extraction conditions for obtaining the extract used in the present invention may vary depending on the solvent used, and thus, there are no particular limitations. For example, when extraction is carried out using water, an alcohol, a water-alcohol mixed liquid, propylene glycol or butylene glycol, it is preferable to subject the plant to immersion or heating to reflux, preferably using 1 to 50 parts by volume of a solvent relative to 1 part by mass of the plant, preferably at a temperature of 3° C. to 100° C., and more preferably 20° C. to 80° C., preferably for one hour to several weeks, and more preferably for 1 day to 30 days. Further, in order to enhance the extraction efficiency, stirring may be performed in addition, or a homogenization treatment may be carried out in a solvent.

Although the extract obtained by performing extraction with the above solvent may be directly used; a fraction having higher activity obtained by further fractionating the extract by an appropriate separating technique such as gel filtration, chromatography or precision distillation can also be used. In the present invention, the term plant extract encompasses various extracts obtained by the methods described above diluted solutions thereof, concentrated solutions thereof, purified products thereof, and dried powders of these extracts.

Further, in the ceramide production enhancer or moisturizer of the present invention, the extract of each plant described above may be used singly, and also, the mixture of two or more kinds of the extracts may be used.

The plant extracts obtained from *Chenopodium hybridum, Melia toosendan, Indigofera tinctoria, Cirsium japonicum, Catalpa ovate*, and *Tagetes erecta* (hereinafter, also called plant extracts of the present invention) have an excellent function to enhance ceramide production as shown in the Examples described below, and a ceramide production enhancer can be obtained by incorporating these extracts therein. Further, since ceramides play an important role in the water holding function or barrier function of the skin as described above, when the ceramide production is enhanced, the ceramide production mechanism of the organism may be returned to normal, the decreased level of ceramides in the stratum corneum may be increased, and a skin having a high barrier function and a high water holding function may be recovered. Therefore, a moisturizer can be obtained by incorporating the plant extracts described above therein.

Furthermore, in recent years, it has been reported that when the production of ceramides in the cells is enhanced, phenomena such as apoptosis, differentiation, and suppression of proliferation are induced. Thus, attention is paid to ceramides as intracellular signaling molecules that control the proliferation, differentiation, apoptosis and the like of cells (see, for example, Sphingolipid targets in cancer therapy, David E. Mordrak, et al., Molecular Cancer Therapeutics, 2006 5(2):pp. 200-8). From these, it can be contemplated that a substance which enhances the production of ceramides can be expected to have an effect of preventing/improving inflammatory diseases and diseases attributable to abnormal proliferation or differentiation of cells, such as malignant tumors, through the suppression of proliferation, induction of differentiation, induction of apoptosis and the like in animal cells. Further, ceramides have a bone resorption inhibitory function, a bone strengthening function, and an alveolar bone loss inhibitory function, and it has also been reported that ceramides are useful for the prevention and improvement of bone and joint diseases such as osteoporosis, bone fracture, lumbago and rheumatism (see, for example, JP-A No. 2001-158736), are effective in the prevention of periodontal diseases (see, for example, JP-A No. 2001-158735), and have an function to impart tension and resilience to hair and improving the feel to touch (see, for example, JP-A No. 10-152421). Therefore, the plant extract of the present invention is also useful for the use in medicines and cosmetic materials intended for the suppression of the proliferation or activation of cancer cells, an enhancement of tension and resilience of hair, the prevention and improvement of bone and joint diseases, and the like.

It has not been known hitherto that plant extracts obtained from *Chenopodium hybridum, Melia toosendan, Indigofera tinctoria, Cirsium japonicum, Catalpa ovata*, and *Tagetes erecta* have a function to enhance ceramide production at all, and this is a new discovery found by the inventors of the present invention.

In the present invention, the plant extract of the present invention obtained from the plants described above may be directly used as a ceramide production enhancer. Alternatively, various additives may be added to the plant extract to the extent that the effects of the plant extract are not affected. For example, appropriate liquid or solid excipients or bulking agents such as titanium oxide, calcium carbonate, distilled water, lactose and starch, may be added to the plant extract, and the resulting mixture may be used as the ceramide production enhancer.

In the case of preparing a composition, the amount of the plant extract in the ceramide production enhancer is not particularly limited, but it is preferable that the extract be contained in an amount of 0.00001% to 20% by mass, and particularly preferably about 0.0001% to 10% by mass, in terms of the solids content.

In the present invention, the extract obtained from the plants described above may be directly used as a moisturizer. Alternatively, the plant extract is incorporated as an active ingredient, and conventionally used additives, other efficacious ingredients and the like are also incorporated to the extent that the effects of the plant extract is not affected, to prepare the moisturizer. For example, a ceramide production enhancer that is already known, a pseudo-ceramide, a natural ceramide, a ceramide saccharide and the like may be incorporated together. Furthermore, an anti-skin aging agent, a whitening agent and the like may be added together as the efficacious ingredients in addition to the ingredients having moisturizing effects.

There are no particular limitations on the ceramide production enhancer already known, but examples include acetylhydroxyproline, potassium glycyrrhizinate, L-camitine, ascorbic acid, ascorbyl glucoside, magnesium ascorbyl phosphate, dl-α-tocopheryl-dl-ascorbyl phosphate, dl-α-tocopheryl phosphate, nicotinic-acid amide, tocopherol nicotinate, L-lactic acid, vitamin C, asparagus extract, Butcher's broom, genkwanin, rosemary, lavender, sage, jujube, black (red) reishi, angelica root, sophora root, coix seed, venetian extract, and rice power extract.

Furthermore, there are no particular limitations on the pseudo-ceramide, but examples include commercially available Ceramide R (manufactured by Unilever PLC), Ceramide PC-104 (manufactured by Amorepacific Corp.), Ceramide HO3 (manufactured by Sederma GmbH), Eldew PS-203 (manufactured by Ajinomoto Co., Inc.), and Sphingolipid E (manufactured by Kao Corp.).

Furthermore, there are no particular limitations on the ceramide saccharide, but examples include glucosylceramide and galactosylceramide, while commercially available examples include Nippn Ceramide (manufactured by Nippon Flour Mills Co., Ltd.), Oryza Ceramide (manufactured by Oryza Oil & Fat Chemical Co., Ltd.), Nissan Ceramide, Neoliquid Ceramide N (manufactured by NOF Corp.), and Ceramide (manufactured by Unitika, Ltd.).

In the case of preparing a composition, the amount of the plant extract in the moisturizer is not particularly limited, but it is preferable that the extract be contained in an amount of 0.00001% to 20% by mass, and more preferably 0.0001% to 10% by mass; in terms of solids content.

Next, a ceramide production enhancer and a moisturizer containing a compound represented by the following Formula (1) as an active ingredient are explained below.

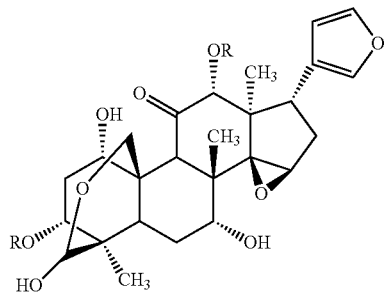

Formula (1)

In Formula (1), R represents an acyl group having 1 to 5 carbon atom(s).

R is preferably an acyl group having 1 to 3 carbon atom(s), and more preferably an acyl group having two carbon atoms. Specific examples of R include a formyl group, an acetyl group, a propionyl group, a butyryl group, an isobutyryl group, a valeryl group and an isovaleryl group. Among them, a formyl group, an acetyl group, and a propionyl group are preferred, and an acetyl group is more preferred. A compound represented by the Formula (1) in which R is an acetyl group is toosendanin, which is a kind of terpene.

The compound represented by the Formula (1) may adopt tautomeric forms as shown below, and the compound represented by the Formula (1) of the present invention encompasses both of the tautomers.

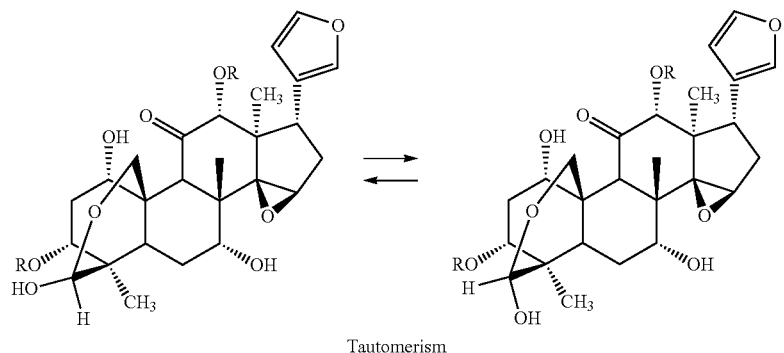

Tautomerism

The method for producing the compound represented by the above Formula (1) used in the present invention is not particularly limited. A chemically synthesized compound may be used, and a compound extracted or purified from a natural product-derived material may also be used. Furthermore, a product that is commercially available as a reagent can also be used.

As the reagent, a product commercially available from Avachem Scientific LLC (USA) and the like can be used.

With regard to the method of obtaining the compound represented by the above Formula (1) from a natural product-derived material, for example, the compound can be isolated from plants such as *Melia toosendan* Sieb. et Zucc., *Melia azedarach*, and *Toona sinensis*.

For these plants, any and all parts (whole tree, whole grass, roots, rhizomes, trunks, branches, stems, leaves, barks, tree sap, tree resin, flowers, fruits, seeds and the like of the plant) can be used. Particularly, in the case of isolating the compound from *Melia toosendan* Sieb. et Zucc., it is preferable to use the barks, seeds or fruits of the plant. Further, an herbal medicine obtained by using the fruits of *Melia toosendan* Sieb. et Zucc. as the original plant, Senrenshi, can also be used. In the case of isolating the compound from *Melia azedarach*, it is preferable to use the barks of the plant. An herbal medicine obtained by using the barks of *Melia azedarach* as the original plant, Kurenpi, can also be used. In the case of isolating the compound from *Toona sinensis*, it is preferable to use the barks of the plant.

The compound represented by the Formula (1) can also be isolated by using these various plants or various parts in appropriate combination.

The method of isolating the compound represented by the above Formula (1) from these plants is not particularly limited, but an example may be a method in which the plant mentioned above is applied to the extraction using an appropriate solvent, and isolating the compound represented by the above Formula (1) from the obtained plant extract by using a technique such as chromatography.

The plant can be used directly or after drying and grinding, for the preparation of the plant extract. As a solvent that is used for the extraction, those conventionally used for the extraction of plant components, for example, water, petroleum ether, n-hexane, toluene, chloroform, ether, ethyl acetate, acetone, methanol, ethanol, propanol, butanol, ethylene glycol, propylene glycol, butylene glycol and mixed solutions thereof, can be used. Further, with regard to the extraction condition, typical extraction conditions can be employed. For example, the above-described plant may be dipped or heated under reflux for two hours to 60 days at 5 to 80° C.

Specific methods for extraction and isolation that can be used include the methods shown in the following Examples, but the present invention is not limited thereto.

The compound represented by the above Formula (1) has an excellent function to enhance ceramide production as shown in the following Examples, and a ceramide production enhancer can be obtained by incorporating this compound therein. Further, as described above, since ceramides have an important function in the moisturizing mechanism or barrier mechanism of the skin, when the ceramide production is enhanced, the ceramide production mechanism of the organism may be returned to normal, the decreased level of ceramides in the stratum corneum may be increased, and a skin having a high barrier function and a high moisturizing function may be recovered. Therefore, a moisturizer can be obtained by incorporating the compound represented by the above Formula (1) therein. It has not been known hitherto that the compound represented by the above Formula (1) has a function to enhance ceramide production at all, and this is a new discovery found by the inventors of the present invention.

In the present invention, the compound represented by the above Formula (1) may be directly used as a ceramide production enhancer. Alternatively, the compound may also be used as a formulation prepared by adding thereto various additives. For example, appropriate liquid or solid excipients or bulking agents such as titanium oxide, calcium carbonate, distilled water, lactose and starch, may be added to the compound, and the resulting mixture may be used as the ceramide production enhancer.

In the case of preparing a composition, the amount of the compound represented by the above Formula (1) in the ceramide production promoter is not particularly limited, but it is preferable that the compound represented by the above Formula (1) be contained in an amount of 0.00001 to 20% by mass, and more preferably 0.0001 to 10% by mass.

In the present invention, the compound represented by the above Formula (1) may be directly used as a moisturizer. Alternatively, the compound represented by the above Formula (1) is incorporated as an active ingredient, and conventionally used additives, other efficacious ingredients and the like may be incorporated to the extent that the effects of the compound are not affected, to prepare the moisturizer. For example, a ceramide production enhancer that is already known, a pseudo-ceramide, a natural ceramide, a ceramide saccharide and the like may be incorporated together. Furthermore, an anti-skin aging agent, a whitening agent and the like may also be added together as the efficacious ingredients in addition to the ingredients having moisturizing effects.

There are no particular limitations on the ceramide production enhancer already known, pseudo-ceramide and ceramide saccharide, and those mentioned as examples in the descriptions on the ceramide production enhancer and moisturizer containing the plant extract as an active ingredient may be used.

In the case of preparing a composition, the amount of the compound represented by the above Formula (1) in the moisturizer is not particularly limited, but it is preferable that the compound represented by the above Formula (1) be contained in an amount of 0.00001 to 20% by mass, and more preferably 0.0001 to 10% by mass.

The moisturizer of the present invention is mostly applied to human beings or animals. This moisturizer encompasses all dosage forms that can be applied to the skin, nails, mucous membranes, hair and the like of a human being or an animal. Examples of the dosage forms of the moisturizer of the present invention include ointments, lotions, creams, beauty essences, skin lotions, massage agents, packs, foundations, lipsticks, bath additives, shampoos, hair conditioners, hair tonics, tablets, capsules, absorbent articles such as sanitary products, and sheet-like products such as bottom wipes and wet tissues. The formulation form of the moisturizer is also not limited, and various formulation forms such as a liquid form, a solid form, an emulsion form, a paste form, a gel form, a powder form, a granule form, a pellet form, and a stick form may be used.

The ceramide production enhancer and moisturizer of the present invention can be applied to the applications such as food products, cosmetic materials and medicinal products.

In the case of using in the food product applications, the ceramide production enhancer and moisturizer can be prepared into general beverage and food products, as well as health beverage and food products, cosmetic beverage and food products, specified health beverage and food products, beverage and food products for patients, and the like, which are based on the concept of the effect of improving and maintaining the moisturization capacity or barrier function of the skin, and optionally have their object displayed thereon.

There are no particular limitations on the form of the food products, and examples include beverages such as fruit juice beverages, milk beverages, and tea beverages; confectionaries such as candies, drops, jellies, cookies, chocolates, cakes, yogurt, and chewing gums; seasonings, cooking oil, dairy products, bread and buns, noodles, and processed rice. Furthermore, the food products may also be cosmetic food products and health food products in the form of tablets, capsules, granules, syrups and the like.

These beverages and food products can be prepared by, for example, using appropriate combinations of additives such as sweeteners, colorants, antioxidants, vitamins, flavors and minerals, and raw materials of food products such as proteins, lipids, saccharides, carbohydrates and vegetable fibers, incorporating the plant extract or the compound represented by the above Formula (1) to this combination, and processing the mixture into various food product forms according to routine methods.

In the case of using in the cosmetic material applications, for example, the ceramide production enhancer and the moisturizer can be prepared into the form of external preparations for skin. In the case of using as the form of an external preparation for skin, the various additives and other efficacious ingredients described above can be appropriately added, in addition to the plant extract or the compound represented by the above Formula (1), and also, those various components that are conventionally used in external preparations for skin can be incorporated in accordance with the formulation form that is employed. Specific examples of the formulation form of the external preparations for skin include various formulation forms capable of being externally applied, such as cream, milky lotion, lotion, gel, ointment, paste, pack, and sheet-like products. When preparing into these formulation forms, for example, various oil agents, surfactants, gelling agents, antiseptics, antioxidants, solvents, alcohols, water, chelating agents, thickeners, ultraviolet absorbents, emulsion stabilizers, pH adjusting agents, pigments, and fragrances can be incorporated.

The content of the plant extract or the compound represented by the above Formula (1) in the external preparation for skin is the same as the amount of the plant extract or the compound represented by the above Formula (1) in the ceramide production enhancer and the moisturizer described above.

The form of administration in the case of using in the applications of medicinal products may be, for example, any of oral administration by means of tablets, capsules, granules, powders, syrups and the like, and parenteral administration by means of injectable preparations, external preparations, suppositories, transdermal absorbents and the like. In the preparation of the medicinal preparations, the ceramide production enhancer of the present invention can be used alone, or can be used in appropriate combination with other pharmaceutically acceptable excipients, binders, extending agents, disintegrants, surfactants, lubricating agents, dispersants, buffering agents, preservatives, flavors, fragrances, film-forming agents, carriers, diluents and the like.

The contents of the plant extract or the compound represented by the above Formula (1) in the preparations are, as a dry solid component, preferably 0.00001% to 20% by mass, and particularly preferably 0.0001% to 10% by mass.

Although the amount of intake or use in the case of using the ceramide production enhancer or moisturizer of the present invention as a food product, a cosmetic material or a medicinal product, can be appropriately selected in accordance with the conditions such as the form, the age and gender of the intaker, usually, it is preferable to take in or use the plant extract or the compound represented by the above Formula (1) in an amount of 0.001 mg to 1000 mg, and it is particularly preferable to take in or use the extract or the compound in an amount of 0.01 mg to 100 mg, per day for an adult.

EXAMPLES

Hereinafter, the present invention is described more in detail with reference to Examples, but the present invention is not limited thereto.

Preparation Example 1

Preparation of Extract of *Chenopodium hybridum*

Was 40 g of the whole grass of *Chenopodium hybridum* (manufactured by Shinwa Bussan Co., Ltd.) finely cut, and 400 mL of 50% ethanol was added thereto. Then, extraction was carried out for 23 days under the conditions of standing at room temperature. Thereafter, the extraction was filtered to obtain 291 mL of a *Chenopodium hybridum* extract. For the extract thus obtained, the evaporation residue was calculated by a method described below, and the evaporation residue was found to be 1.73 (w/v %).
<Calculation of Evaporation Residue>
Was 1000 μl of the *Chenopodium hybridum* extract was dried for 6 hours at 105° C. (dryer: DRY Thermo Unit DTU-1C (manufactured by Taitec Corporation) was used), and thus, 17.3 mg of a dried product was obtained. The evaporation residue of this extract was calculated by the formula: 17.3/1000×100=1.73 (w/v %). In the Preparation Examples described below, the evaporation residue of each extract were calculated in the same manner.

Preparation Example 2

Preparation of Extract of *Melia toosendan*

Was 40 g of the fruits of *Melia toosendan* (manufactured by Shinwa Bussan Co., Ltd.) finely cut, and 400 mL of 50% ethanol was added thereto. Then, extraction was carried out for 23 days under the conditions of standing at room temperature. Thereafter, the extract was filtered to obtain 328 mL of a *Melia toosendan* extract (evaporation residue 1.68 (w/v %)).

Preparation Example 3

Preparation of Extract of *Indigofera tinctoria*

Was 40 g of the dried pigments of the leaves of *Indigofera tinctoria* (manufactured by Shinwa Bussan Co., Ltd. finely cut, and 400 mL of 50% ethanol was added thereto. Then, extraction was carried out for 23 days under the conditions of standing at room temperature. Thereafter, the extract was filtered to obtain 347 mL of a *Indigofera tinctoria* extract (evaporation residue 0.72 (w/v %)).

Preparation Example 4

Preparation of Extract of *Cirsium japonicum*

Was 40 g of the roots of *Cirsium japonicum* (manufactured by Shinwa Bussan Co., Ltd. finely cut, and 400 mL of 50% ethanol was added thereto. Then, extraction was carried out for 23 days under the conditions of standing at room temperature. Thereafter, the extract was filtered to obtain 272 mL of a *Cirsium japonicum* extract (evaporation residue 0.9 (w/v %)).

Preparation Example 5

Preparation of Extract of *Catalpa ovata*

Was 40 g of the fruits of *Catalpa ovata* (manufactured by Shinwa Bussan Co., Ltd. was finely cut, and 400 mL of 50% ethanol was added thereto. Then, extraction was carried out for 23 days under the conditions of standing at room temperature. Thereafter, the extract was filtered to obtain 332 mL of a *Catalpa ovata* extract (evaporation residue 1.39 (w/v %)).

Preparation Example 6

Preparation of Extract of *Tagetes erecta*

Was 40 g of the flowers of *Tagetes erecta* (manufactured by Shinwa Bussan Co., Ltd. finely cut, and 400 mL of 50% ethanol was added thereto. Then, extraction was carried out for 23 days under the conditions of standing at room temperature. Thereafter, the extract was filtered to obtain 262 mL of a *Tagetes erecta* extract (evaporation residue 2.86 (w/v %)).

Test Example 1

Verification of Ceramide Production Enhancing Effect

Normal human epidermal keratinocytes (trade name: NHEK(F), manufactured by Kurabo Industries, Ltd.) were cultured under the conditions of 37° C. and 5% $CO_2$, in a culture medium (trade name: EpiLife-KG2, manufactured by Kurabo Industries, Ltd.) using a culture plate.

Thereafter, the culture medium was exchanged with EpiLife-KG2 without growth factors such as epidermal growth factor, and a dilution prepared from each of the extracts prepared in the Preparation Examples described above, the concentration of which was adjusted to 1 w/v % in terms of solids content, or a control solution (50% ethanol) was added to the culture fluid in an amount of 0.1%.

The cells were cultured for 3 days, and then the respective cells were collected from each well.

An organic phase, contained lipids extracted from the collected cells by the Blight and Dyer method, was transferred into a glass tube, and was dried to solid in nitrogen stream. Subsequently, the dried product was redissolved in chloroform and methanol, and this was used as a lipid sample.

Further, 0.1N NaOH and a 1% aqueous SDS solution were added to the cells from which lipids had been extracted, and the mixture was heated at 60° C. for 2 hours to thereby solubilize proteins. The mixture was cooled to room temperature, and then 2N HCl was added for neutralization. The amount of proteins was quantified by the BCA method.

The lipid sample thus prepared was developed two times in a horizontal position by thin layer chromatography (TLC) using chloroform:methanol:acetic acid=190:9:1. A copper sulfate solution was sprayed, followed by baking on a hot plate, to thereby detect ceramides. This was designated as the amount of ceramides.

The results are shown in FIG. 1. Meanwhile, the vertical axis of the graph shown in FIG. 1 represents the relative values in the case where the amount of ceramides of the control solution-added group Was designated as 1.

As is obvious from FIG. 1, in the systems to which extracts of *Chenopodium hybridum*, *Melia toosendan*, *Indigofera tinctoria*, *Cirsium japonicum*, *Catalpa ovata*, and *Tagetes erecta* were added, it was recognized that the amounts of ceramide increased as compared to the control.

Therefore, it was found that the ceramide production enhancers of the present invention containing these plant extracts as active ingredients, can enhance ceramide production. Furthermore, since ceramides participate in the maintenance of water holding function and barrier function of the skin, it was found from the results of FIG. 1 that the plant extracts of the present invention enhances the production of ceramides and have a moisturizing function.

Preparation Example 7

Isolation of Component Having an Activity to Enhance Ceramide Production

Eight hundred g of the fruits of *Melia toosendan* (Senrenshi, manufactured by Shinwa Bussan Co., Ltd.) were extracted with 8 L of 50% ethanol at 20 to 35° C. for 7 days, and the solvent was concentrated. Thus, 123.5 g of an extracted solid fraction was obtained. The obtained extracted solid fraction was fractionated based on the enhancing activity of ceramide production assayed according to the test example described below. Liquid-liquid distribution was carried out by using water and ethyl acetate, and the inhibitory activity was concentrated in 20.78 g of the ethyl acetate layer (yield 16.8%). The ethyl acetate layer was further fractionated by silica gel column chromatography, and thus Fraction (1) 7.49 g was obtained (yield 6.1%). Fraction (1) was further fractionated using silica gel column chromatography, and thus Fraction (2) 2.78 g was obtained (yield 2.3%). Subsequently, this traction was fractionated using LH-20 (Sephadex (trade mark) LH20, manufactured by GE Healthcare Inc.), and thus Fraction (3) 1.28 g was obtained (yield 1.0%). 340 mg of Fraction (3) was fractionated by HPLC, and thus Fraction (4) 164.8 mg was obtained (yield 0.48%). Furthermore, 20 mg of Fraction (4) was fractionated by HPLC, and thus Fraction (5) 1.4 mg was obtained (yield 0.03%)) Fraction (5) was subjected to a structure analysis using NMR. In the structure analysis based on NMR, toosendanin which is commercially available as a reagent (manufactured Avachem Scientific LLC) was used for comparison. The results of the structure analysis based on NMR are presented in Table 1.

As a result, the active component isolated from *Melia toosendan* was a compound having a structure shown in the following Table 1, and this compound was identified as toosendanin. In Table 1, the abbreviation Ac represents an acetyl group.

TABLE 1

| | 13C-NMR (ppm) | | 1H-NMR (ppm) | |
|---|---|---|---|---|
| | Isolated component | Toosendanin (reagent) | Isolated component | Toosendanin (reagent) |
| 1 | 70.7 | 70.7 | 4.24 | 4.24 |
| 2 | 37.2 | 37.2 | 1.8 | 1.8 |
| | | | 2.73 | 2.73 |
| 3 | 74.8 | 74.8 | 5.19 | 5.19 |
| 4 | 41.2 | 41.2 | — | — |
| 5 | 29.6 | 29.6 | 2.8 | 2.8 |
| 6 | 26.2 | 26.2 | 1.71 | 1.71 |
| | | | 2 | 2 |
| 7 | 70.8 | 70.9 | 3.57 | 3.57 |
| 8 | 43.9 | 43.9 | — | — |
| 9 | 50.1 | 50.1 | 4.7 | 4.7 |
| 10 | 42.9 | 42.9 | — | — |
| 11 | 209.1 | 209.1 | — | — |
| 12 | 79.7 | 79.7 | 5.33 | 5.33 |
| 13 | 46.9 | 46.9 | — | — |
| 14 | 73.6 | 73.6 | — | — |
| 15 | 60 | 60 | 3.81 | 3.8 |
| 16 | 34.8 | 34.8 | 2.02 | 2.01 |
| | | | 2.11 | 2.11 |
| 17 | 39.9 | 39.9 | 2.88 | 2.88 |
| 18 | 15.9 | 15.8 | 1.37 | 1.38 |
| 19 | 65.5 | 65.5 | 4.25 | 4.24 |
| | | | 4.31 | 4.31 |
| 20 | 124.3 | 124.3 | — | — |
| 21 | 142.1 | 142.1 | 7.2 | 7.2 |
| 22 | 113 | 113 | 6.16 | 6.16 |
| 23 | 143.7 | 143.7 | 7.4 | 7.4 |
| 28 | 20 | 20 | 0.84 | 0.84 |
| 29 | 97.2 | 97.2 | 4.83 | 4.83 |
| 30 | 23.1 | 23.2 | 1.12 | 1.12 |
| AcO | 21.4 | 21.4 | 2.07 | 2.07 |
| | 172.9 | 172.9 | — | — |
| | 20.9 | 20.9 | 1.94 | 1.95 |
| | 172.2 | 172.2 | — | — |

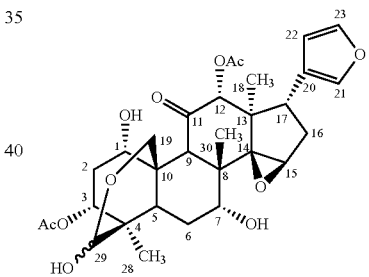

Test Example 2

Verification of Ceramide Production Enhancing Effect

Normal human epidermal keratinocytes (trade name: NHEK(F), manufactured by Kurabo Industries, Ltd.) were cultured under the conditions of 37° C. and 5% $CO_2$, in a culture fluid (trade name: EpiLife-KG2, manufactured by Kurabo Industries, Ltd.) using a culture plate.

Thereafter, the culture fluid was exchanged with EpiLife-KG2 from which growth factors such as epidermal growth factor had been eliminated, and a solution in which concentration of toosendanin was adjusted to 1 mM (574 ppm), or a control solution (50% ethanol) was added to the culture fluid in an amount of 0.01%.

The cells were cultured for 3 days, and then the respective cells were collected from each well.

An organic phase obtained by extracting lipids from the collected cells by the Blight and Dyer method, was transferred into a glass tube, and was dried to solid in nitrogen stream. Subsequently, the dried product was redissolved in chloroform and methanol, and this was used as a lipid sample.

Further, 0.1N NaOH and a 1% aqueous SDS solution were added to the cells from which lipids had been extracted, and the mixture was heated at 60° C. for 2 hours to thereby solubilize proteins. The mixture was cooled to room temperature, and then 2N HCl was added for neutralization. The amount of proteins was quantified by the BCA method.

The lipid sample thus prepared was developed two times in a horizontal position by thin layer chromatography (TLC) using chloroform:methanol:acetic acid 190:9:1. A copper sulfate solution was sprayed, followed by baking on a hot plate, to thereby detect ceramides. This was designated as the amount of ceramides.

The results are shown in Table 2. Meanwhile, the amounts of ceramides shown in Table 2 indicate relative values in the case where the amount of ceramides of the control solution-added group was designated as 1.

Reference Example

1. Preparation of Extract of *Eucalyptus*

Forty g of the leaves of *Eucalyptus globulus* Labillardiere (manufactured by Shinwa Bussan Co., Ltd. were finely cut, and 400 mL of 50% ethanol was added thereto. Then, extraction was carried out for 7 days under the conditions of standing at room temperature. Thereafter, the extract was filtered to obtain 291 mL of a *Eucalyptus globulus* Labillardiere extract (evaporation residue 3.16% (w/v)).

2. Verification of Ceramide Production Enhancing Effect

The ceramide production enhancing effect was verified according to the same procedures used in Test Example 2, using the *Eucalyptus* extract thus obtained. Meanwhile, the addition to the cells was carried out such that an extract, the concentration of which was adjusted to be 1% (w/v) in terms of solids content, was added in an amount of 0.001%.

The results are shown in Table 2. Meanwhile, the *Eucalyptus* extract has been well known as a moisturizing component having a ceramide production enhancing function.

TABLE 2

| | Concentration for verification | Amount of ceramide production (Amount of ceramide production of control solution-added group = 1) | Remarks |
| --- | --- | --- | --- |
| Toosendanin | 57.4 ppb | 1.22 | Present invention |
| *Eucalyptus* extract | 100 ppb | 1.24 | Reference example |

As is obvious from Table 2, in the system to which toosendanin was added, an increase in the amount of ceramide production was recognized as compared to the control system. Thus, it was understood that the ceramide production enhancer of the present invention containing the compound represented by the above Formula (1) as an active ingredient, can enhance ceramide production.

Furthermore, since ceramides participate in the maintenance of the moisturizing function and barrier function of the skin, it can be seen from the results of Table 2 that the compound represented by the above Formula (1) enhances the production of ceramides and has a moisturizing function. That is, similar to the *Eucalyptus extract* (Reference Example), which is a known moisturizing component, the moisturizer of the present invention containing the compound represented by the above Formula (1) as an active ingredient, is an agent which enhances the production of ceramides and has a moisturizing function.

Prescription Example 1

Using the extracts obtained by the Preparation Examples 1 to 6 as active ingredients, a skin lotion, an O/W (oil-in-water) type milky lotion, a W/O (water-in-oil) type cream, a gel-type cosmetics, and a liquid bath additive, each having the composition described below, were prepared by routine methods.

1-1. Preparation of Skin Lotion 1

| (Composition) | (Amount: mass %) |
| --- | --- |
| Extract of *Chenopodium hybridum* | 3.00 |
| Plyethylene glycol (trade name: PEG-1540, manufactured by Sanyo Chemical Industries, Ltd.) | 1.00 |
| Polyoxyethylene(20) sorbitan monolauric acid ester | 1.50 |
| Glycerin | 2.00 |
| Paraben | 0.10 |
| Purified water | remnant |

1-2. Preparation of Skin Lotion 2

| (Composition) | (Amount: mass %) |
| --- | --- |
| Extract of *Melia toosendan* | 3.00 |
| Plyethylene glycol (trade name: PEG-1540, manufactured by Sanyo Chemical Industries, Ltd.) | 1.00 |
| Polyoxyethylene(20) sorbitan monolauric acid ester | 1.50 |
| Glycerin | 2.00 |
| Paraben | 0.10 |
| Purified water | remnant |

2-1. Preparation of O/W Type Milky Lotion 1

| (Composition) | (Amount: mass %) |
| --- | --- |
| Extract of *Indigofera tinctoria* | 3.00 |
| Plyethylene glycol (trade name: PEG-2000, manufactured by Sanyo Chemical Industries, Ltd.) | 1.00 |
| Pullulan (Product name: Pullulan PT-20, manufactured by Hayashibara Co., Ltd.) | 0.40 |
| Cetyl alcohol | 1.00 |
| Petrolatum | 2.00 |
| Scualane | 6.00 |
| Dimethylpolysiloxane | 2.00 |
| Glycerin | 2.00 |
| Pseudo-ceramide (N-(3-hexadecyloxy-2-hydroxypropyl)-N-2-hydroxyethylhexadecanamide) | 1.00 |
| Polyoxyethylene(10) monooleic acid ester | 1.00 |
| Glycerol monostearic acid ester | 1.00 |
| Acidic heteropolysaccharides derived from the callus of a plant (1 wt % aqueous solution of tuberose polysaccharide) | 2.00 |
| Paraben | 0.20 |
| Purified water | remnant |

2-2. Preparation of O/W Type Milky Lotion 2

| (Composition) | (Amount: mass %) |
|---|---|
| Extract of *Cirsium japonicum* | 3.00 |
| Plyethylene glycol (trade name: PEG-2000, manufactured by Sanyo Chemical Industries, Ltd.) | 1.00 |
| Pullulan (Product name: Pullulan PT-20, manufactured by Hayashibara Co., Ltd.) | 0.40 |
| Cetyl alcohol | 1.00 |
| Petrolatum | 2.00 |
| Scualane | 6.00 |
| Dimethylpolysiloxane | 2.00 |
| Glycerin | 2.00 |
| Pseudo-ceramide (N-(3-hexadecyloxy-2-hydroxypropyl)-N-2-hydroxyethylhexadecanamide) | 1.00 |
| Polyoxyethylene(10) monooleic acid ester | 1.00 |
| Glycerol monostearic acid ester | 1.00 |
| Acidic heteropolysaccharides derived from the callus of a plant (1 wt % aqueous solution of tuberose polysaccharide) | 2.00 |
| Paraben | 0.20 |
| Purified water | remnant |

3-1. Preparation of W/O Type Cream 1

| (Composition) | (Amount: mass %) |
|---|---|
| Extract of *Catalpa ovata* | 3.00 |
| Alkyl acrylate copolymer (trade name: Yodosol GH810, manufactured by Kanebo NSC, Ltd.) | 1.30 |
| Polyvinylpyrrolidone (trade name: Rubiscol K-90, manufactured by BASE Japan, Ltd.) | 0.70 |
| Dimethylpolysiloxane | 10.00 |
| methylphenylpolysiloxane | 3.00 |
| Octamethylcyclotetrasiloxane | 12.00 |
| Polyoxyalkylene-modified silicone | 5.00 |
| 1,3-butylene glycol | 6.00 |
| Pseudo-ceramide (N-(3-hexadecyloxy-2-hydroxypropyl)-N-2-hydroxyethylhexadecanamide) | 1.20 |
| Paraben | 0.20 |
| Fragrance | minute amount |
| Purified water | remnant |

3-2. Preparation of W/O Type Cream 2

| (Composition) | (Amount: mass %) |
|---|---|
| Extract of *Tagetes erecta* | 3.00 |
| Alkyl acrylate copolymer (trade name: Yodosol GH810, manufactured by Kanebo NSC, Ltd.) | 1.30 |
| Polyvinylpyrrolidone (trade name: Rubiscol K-90, manufactured by BASE Japan, Ltd.) | 0.70 |
| Dimethylpolysiloxane | 10.00 |
| methylphenylpolysiloxane | 3.00 |
| Octamethylcyclotetrasiloxane | 12.00 |
| Polyoxyalkylene-modified silicone | 5.00 |
| 1,3-butylene glycol | 6.00 |
| Pseudo-ceramide (N-(3-hexadecyloxy-2-hydroxypropyl)-N-2-hydroxyethylhexadecanamide) | 1.20 |
| Paraben | 0.20 |
| fragrance | minute amount |
| Purified water | remnant |

4-1. Preparation of Gel-Type Cosmetics 1

| (Composition) | (Amount: mass %) |
|---|---|
| Extract of *Chenopodium hybridum* | 1.00 |
| Plyethylene glycol (trade name: PEG-2000, manufactured by Sanyo Chemical Industries, Ltd.) | 0.50 |
| Xanthane gum (trade name: Neosoft XKK, manufactured by KOHJIN Co., Ltd.) | 0.20 |
| Glycerin | 3.00 |
| Ethanol | 3.00 |
| Carboxyvinyl polymer | 0.50 |
| potassium hydroxide | 0.15 |
| Polyoxyethylene hardened castor oil | 1.00 |
| Citric acid | 0.80 |
| Trisodium citrate | 0.80 |
| Nylon powder | 1.00 |
| Paraben | 0.10 |
| Fragrance | minute amount |
| Purified water | remnant |

| (Composition) | (Amount: mass %) |
|---|---|
| Extract of *Melia toosendan* | 1.00 |
| Plyethylene glycol (trade name: PEG-2000, manufactured by Sanyo Chemical Industries, Ltd.) | 0.50 |
| Xanthane gum (trade name: Neosoft XKK, manufactured by KOHJIN Co., Ltd.) | 0.20 |
| Glycerin | 3.00 |
| Ethanol | 3.00 |
| Carboxyvinyl polymer | 0.50 |
| potassium hydroxide | 0.15 |
| Polyoxyethylene hardened castor oil | 1.00 |
| Citric acid | 0.80 |
| Trisodium citrate | 0.80 |
| Nylon powder | 1.00 |
| Paraben | 0.10 |
| Fragrance | minute amount |
| Purified water | remnant |

5-1. Preparation of Liquid Bath Additive 1

| (Composition) | (Amount: mass %) |
|---|---|
| Extract of *Indigofera tinctoria* | 3.00 |
| Pseudo-ceramide (N-(3-hexadecyloxy-2-hydroxypropyl)-N-2-hydroxyethylhexadecanamide) | 0.10 |
| Isopropyl myristate | 15.00 |
| Polyoxyethylene(12) oleyl ether | 10.00 |
| Polyoxyethylene(6) oleic acid ester | 6.00 |
| Acidic heteropolysaccharides derived from the callus of a plant (1 wt % aqueous solution of tuberose polysaccharide) | 2.00 |
| Paraben | 0.20 |
| Fragrance | minute amount |
| liquid paraffin | remnant |

5-2. Preparation of Liquid Bath Additive 2

| (Composition) | (Amount: mass %) |
|---|---|
| Extract of *Cirsium japonicum* | 3.00 |
| Pseudo-ceramide (N-(3-hexadecyloxy-2-hydroxypropyl)-N-2-hydroxyethylhexadecanamide) | 0.10 |

| (Composition) | (Amount: mass %) |
|---|---|
| Isopropyl myristate | 15.00 |
| Polyoxyethylene(12) oleil ether | 10.00 |
| Polyoxyethylene(6) oleil ether | 6.00 |
| Acidic heteropolysaccharides derived from the callus of a plant (1 wt % aqueous solution of tuberose polysaccharide) | 2.00 |
| Paraben | 0.30 |
| Fragrance | minute amount |
| liquid paraffin | remnant |

Prescription Example 2

A skin lotion, an O/W (oil-in-water) type milky lotion, a W/O (water-in-oil) type cream, a gel-type cosmetics, a liquid bath additive and a food product in a tablet form, each having the composition described below, were prepared using toosendanin as an active ingredient, by routine methods.

1. Preparation of Lotion

| (Composition) | (Amount: mass %) |
|---|---|
| Toosendanin (manufactured by AvaChem Scientific LLC) | 0.05 |
| Plyethylene glycol (trade name: PEG-1540, manufactured by Sanyo Chemical Industries, Ltd.) | 1.00 |
| Polyoxyethylene(20) sorbitan monolauric acid ester | 1.50 |
| Glycerin | 2.00 |
| Paraben | 0.10 |
| Purified water | remnant |

2. Preparation of O/W Type Milky Lotion

| (Composition) | (Amount: mass %) |
|---|---|
| Toosendanin (manufactured by AvaChem Scientific LLC) | 1.00 |
| Plyethylene glycol (trade name: PEG-2000, manufactured by Sanyo Chemical Industries, Ltd.) | 1.00 |
| Pullulan (Product name: Pullulan PT-20, manufactured by Hayashibara Co., Ltd.) | 0.40 |
| Cetyl alcohol | 1.00 |
| Petrolatum | 2.00 |
| Scualane | 6.00 |
| Dimethylpolysiloxane | 2.00 |
| Glycerin | 2.00 |
| Pseudo-ceramide (N-(3-hexadecyloxy-2-hydroxypropyl)-N-2-hydroxyethylhexadecanamide) | 1.00 |
| Polyoxyethylene(10) monooleic acid ester | 1.00 |
| Glycerol monostearic acid ester | 1.00 |
| Acidic heteropolysaccharides derived from the callus of a plant (1 wt % aqueous solution of tuberose polysaccharide) | 2.00 |
| Paraben | 0.20 |
| Purified water | remnant |

3. Preparation of W/O Type Cream

| (Composition) | (Amount: mass %) |
|---|---|
| Toosendanin (manufactured by AvaChem Scientific LLC) | 3.00 |
| Alkyl acrylate copolymer (trade name: Yodosol GH810, manufactured by Kanebo NSC, Ltd.) | 1.30 |
| Polyvinylpyrrolidone (trade name: Rubiscol K-90, manufactured by BASE Japan, Ltd.) | 0.70 |
| Dimethylpolysiloxane | 10.00 |
| methylphenylpolysiloxane | 3.00 |
| Octamethylcyclotetrasiloxane | 12.00 |
| Polyoxyalkylene-modified silicone | 5.00 |
| 1,3-butylene glycol | 6.00 |
| Pseudo-ceramide (N-(3-hexadecyloxy-2-hydroxypropyl)-N-2-hydroxyethylhexadecanamide) | 1.20 |
| Paraben | 0.20 |
| Fragrance | minute amount |
| Purified water | remnant |

4. Preparation of Gel Type Cosmetics

| (Composition) | (Amount: mass %) |
|---|---|
| Toosendanin (manufactured by AvaChem Scientific LLC) | 0.50 |
| Plyethylene glycol (trade name: PEG-2000, manufactured by Sanyo Chemical Industries, Ltd.) | 0.50 |
| Xanthane gum (trade name: Neosoft XKK, manufactured by KOHJIN Co., Ltd.) | 0.20 |
| Glycerin | 3.00 |
| Ethanol | 3.00 |
| Carboxyvinyl polymer | 0.50 |
| potassium hydroxide | 0.15 |
| Polyoxyethylene hardened castor oil | 1.00 |
| Citric acid | 0.80 |
| Trisodium citrate | 0.80 |
| Nylon powder | 1.00 |
| Paraben | 0.10 |
| Fragrance | minute amount |
| Purified water | remnant |

5. Preparation of Liquid Bath Additive

| (Composition) | (Amount: mass %) |
|---|---|
| Toosendanin (manufactured by AvaChem Scientific LLC) | 0.01 |
| Pseudo-ceramide (N-(3-hexadecyloxy-2-hydroxypropyl)-N-2-hydroxyethylhexadecanamide) | 0.10 |
| Isopropyl myristate | 15.00 |
| Polyoxyethylene(12) oleyl ether | 10.00 |
| Polyoxyethylene(6) oleic acid ester | 6.00 |
| Acidic heteropolysaccharides derived from the callus of a plant (1 wt % aqueous solution of tuberose polysaccharide) | 2.00 |
| Paraben | 0.30 |
| Fragrance | minute amount |
| liquid paraffin | remnant |

6. Preparation of Food

Each material is mixed according to the composition described below, and form them into tablet.

| (Composition) | (Amount: mass %) |
|---|---|
| Toosendanin (manufactured by AvaChem Scientific LLC) | 1.0 |
| Crystalline cellulose | 89.0 |
| Whey calcium | remnant |

INDUSTRIAL APPLICABILITY

The ceramide production enhancer and the moisturizer of the present invention have functions to enhance ceramide production. Therefore, the present invention can be utilized in the fields of cosmetics, functional foods, medicinal products and medical treatments.

Having described our invention as related to the present embodiments, it is our intention that the invention not be limited by any of the details of the description, unless otherwise specified, but rather be construed broadly within its spirit and scope as set out in the accompanying claims.

This application claims priority on Patent Application No. 2009-231847 filed in Japan on Oct. 5, 2009 and Patent Application No. 2010-103651 filed in Japan on Apr. 28, 2010, which are entirely herein incorporated by reference.

The invention claimed is:

1. A method of increasing the amount of ceramide in dry human skin, comprising
   applying an extract of *Melia toosendan* to dry human skin that is need of an increase in the amount of ceramide, and
   increasing the amount of ceramide in said skin as a result of said applying,
   wherein the extract of *Melia toosendan* is an extract of the fruit or seed of said *Melia toosendan*.

2. The method of claim 1, wherein said extract is an extract of the fruit of *Melia toosendan*.

3. The method of claim 1, wherein the dry skin in need of the increase in ceramide production is characterized by a decreased amount of ceramide in the stratum corneum as compared to skin that is not dry.

4. The method of claim 1, wherein said extract is an extract of the seed of *Melia toosendan*.

5. The method of claim 1, wherein the extract is a water, ethanol or aqueous ethanol extract.

6. The method of claim 5, wherein the extract is an aqueous ethanol extract.

7. A method of moisturizing dry human skin by increasing the amount of ceramide in the skin, comprising
   applying an extract of *Melia toosendan* to dry human skin that is in need of moisturizing, increasing the amount of ceramide in said skin as a result of said applying, and moisturizing said skin as a result of said increasing of the amount of said ceramide,
   wherein the extract of *Melia toosendan* is an extract of the fruit or seed of said *Melia toosendan*.

8. The method of claim 7, wherein said extract is an extract of the fruit of *Melia toosendan*.

9. The method of claim 7, wherein the dry skin in need of moisturizing is characterized by a decreased amount of ceramide in the stratum corneum as compared to skin that is not dry.

10. The method of claim 7, wherein said extract is an extract of the seed of *Melia toosendan*.

11. The method of claim 7, wherein the extract is a water, ethanol or aqueous ethanol extract.

12. The method of claim 11, wherein the extract is an aqueous ethanol extract.

13. A method of increasing the amount of ceramide in dry human skin, comprising
   (a) applying an extract of the fruit or seed of *Melia toosendan* to dry human skin that is in need of an increase in the amount of ceramide,
   wherein the dry skin in which the amount of ceramide is to be increased is characterized by a decreased amount of ceramide in the stratum corneum as compared to skin that is not dry, wherein the extract is a water, ethanol or aqueous ethanol extract, and
   (b) increasing the amount of ceramide in said dry skin as a result of the applying.

14. A method of moisturizing dry human skin by increasing the amount of ceramide, comprising
   (a) applying an extract of the fruit or seed of *Melia toosendan* to dry human skin that is in need of being moisturized and is in need of an increase in the amount of ceramide in the skin, wherein the dry skin that is in need of an increase in the amount of ceramide is characterized by a decreased amount of ceramide in the stratum corneum as compared to skin that is not dry, wherein the extract is a water, ethanol or aqueous ethanol extract,
   (b) increasing the amount of ceramide in said skin as a result of the applying; and
   (c) moisturizing said dry skin as a result of said increasing of the amount of said ceramide.

* * * * *